(12) United States Patent
Brhel

(10) Patent No.: US 7,020,901 B2
(45) Date of Patent: Apr. 4, 2006

(54) EYE AND EAR PROTECTION APPARATUS

(76) Inventor: Joseph A. Brhel, 4530 S. Packard Ave., Cudahy, WI (US) 53110

( * ) Notice: Subject to any disclaimer, the term of this patent is extended or adjusted under 35 U.S.C. 154(b) by 253 days.

(21) Appl. No.: 10/604,432

(22) Filed: Jul. 21, 2003

(65) Prior Publication Data
US 2005/0015852 A1 Jan. 27, 2005

(51) Int. Cl.
A42B 1/06 (2006.01)
(52) U.S. Cl. .......................... 2/209; 351/158
(58) Field of Classification Search ............ 2/10, 2/12, 13, 426, 209, 423, 422; 351/158
See application file for complete search history.

(56) References Cited

U.S. PATENT DOCUMENTS

| 2,861,274 | A | * | 11/1958 | Stuart et al. | 2/6.7 |
| 4,802,243 | A | * | 2/1989 | Griffiths | 2/422 |
| 4,856,089 | A | | 8/1989 | Horton | 455/351 |
| 5,133,596 | A | | 7/1992 | Korny et al. | 351/158 |
| 5,179,736 | A | * | 1/1993 | Scanlon | 2/209 |
| 5,278,999 | A | | 1/1994 | Brown et al. | 2/209 |
| 5,373,583 | A | * | 12/1994 | Birum | 2/10 |
| 5,546,610 | A | * | 8/1996 | Herzig et al. | 2/422 |
| 5,724,119 | A | * | 3/1998 | Leight | 351/158 |
| 6,082,857 | A | * | 7/2000 | Lockhart | 351/178 |
| 6,138,286 | A | * | 10/2000 | Robrahn et al. | 2/436 |
| 6,511,177 | B1 | * | 1/2003 | Hall et al. | 351/158 |

* cited by examiner

Primary Examiner—Katherine M. Moran
(74) Attorney, Agent, or Firm—Joseph S. Heino

(57) ABSTRACT

A combined eye and ear protective device has an eye protective portion and an ear protective portion, the eye protective portion and the ear protective portion being functionally cooperating. The protective device utilizes the eye protective portion of the device as the head support for the ear protective portion of the device and configures the eye protective portion within a single piece of optically clear material that reduces or eliminates the discontinuity between the lenses and frame of conventional eyeglasses and provides for unimpeded peripheral vision. A one piece polycarbonate resin eye protective portion is coupled with the ear protective portion to allow the eye protective portion to move between a "down" position and an "up" position.

13 Claims, 4 Drawing Sheets

EYE AND EAR PROTECTION APPARATUS

BACKGROUND OF INVENTION

This invention relates generally to protective devices used by human beings. More particularly, it relates to an apparatus that is configured to provide both protection for a user's eyes and ears by use of the same device.

Eye protective devices have been around for many years and are old art. Such devices find use in the workplace by millions of workers every day. Protective eyeglasses are indeed mandated by federal and state safety standards in factory settings and manufacturing facilities. Eyeglass frames having separate protective lenses are most often used. Other specialized eye protective devices have been devised for welders, painters, and other industrial professionals and often take the form of an eye and face shield. When such devices are not in use, they may simply be removed and stowed away for later use. Other configurations allow for the eye protective device to be rotatably moveable away from and out of the user's visual field. It is also understood that such eye protective devices are not limited to use in the workplace. They may be used by sportspersons, law enforcement personnel, military personnel, airport employees and other persons who need to protect their eyes without substantially impairing their visual acuity.

Similarly, ear protective devices have been around for many years and are old art as well. Sound muffling devices find use in the workplace by millions of workers every day and are likewise required by federal and state safety standards. Such devices may be in the form of sound deadening ear plugs, ear muffs, and other like hearing protection. When such devices are not in use, they may also be removed. And their use is not limited to the workplace either. As was alluded to above, they may be used by others who similarly need to protect their ears during certain activities when hearing could be impaired.

In the experience of this inventor, the wearing of a separate eye protective device with a separate ear protective device can be uncomfortable. For example, the use of earmuff ear protectors very often has the tendency of "pinching" the skull grips of conventional glasses, especially behind the user's ears. This can be particularly uncomfortable when the user is wearing safety glasses over regular corrective glasses. This discomfort makes the user more apt to wear one or the other of the protective devices. Additionally, conventional glasses may need to be removed intermittently for close-up, unimpeded visualization. Wearing earmuff ear protectors makes this an inconvenient proposition and also one that compromises the safety of the user when the user removes either protective device. Furthermore, the use of conventional safety glasses with earmuff ear protectors has a tendency to break a portion of the earmuff seal about the user's ears thereby rendering the hearing protection afforded by the ear protectors less effective.

There have been prior attempts to combine the concept of eye protection with ear protection. Such attempts are disclosed in U.S. Pat. No. 4,856,089 issued to Horton, U.S. Pat. No. 5,133,596 issued to Korny et al., and U.S. Pat. No. 5,278,999 issued to Brown et al. In the experience of this inventor, such devices have practical limitations that are not readily apparent until the devices are placed into practice. For example, such devices utilize a combined ear and eye protection configuration. The devices may be constructed with an ear protection portion which includes a head support member that is independent of the eye protection portion of the device. This adds to the complexity of the device as well as increased costs of production. In devices that attempt to utilize the eye protection portion of the device as the head support for the ear protection portion, the eye protection portion tends to be configured in the fashion of conventional eyeglasses that include a frame and lenses that are separate and apart from each other. In the view of this inventor, what is needed is a combined ear and eye protection device that utilizes the eye protection portion of the device as the head support for the ear protection portion, but that configures the eye protection portion in such a way that improves on the conventional eyeglass configuration by use of a single piece of eye protection material.

Accordingly, it is an object of the present invention to provide a new and useful combined ear and eye protection device that utilizes the eye protection portion of the device as the head support for the ear protection portion of the device and that configures the eye protection portion in a way that improves on the conventional eyeglass configuration by using a single piece of eye protection material in a unitary configuration. It is another object of the present invention to provide such a combined ear and eye protection device that configures the eye protection portion in a single piece manufacture that reduces or eliminates the discontinuity between lens and frame. It is still another object of the present invention to provide such a combined ear and eye protection device that reduces or eliminates any impairment of the user's field of view and that enhances it by providing for unimpeded peripheral vision. It is yet another object of the present invention to provide such a protective device that utilizes a minimal number of elements by incorporating a unitary, one piece eye protector with a pair of ear muffs and that requires only a minimal number of steps to use. It is a further object of the present invention to provide such a protective device that is easy to assemble, economical to manufacture and that can be manufactured in a variety of lenses.

SUMMARY OF INVENTION

The protective apparatus of the present invention has obtained these objects. It provides for a combined eye and ear protective device that has an eye protective portion and an ear protective portion, the eye protective portion and the ear protective portion being functionally cooperating. In the preferred embodiment of the present invention, the protective device utilizes the eye protective portion of the device as the head support for the ear protective portion of the device and configures the eye protective portion in a way that improves on the conventional eyeglass configuration. This combined ear and eye protective device configures the eye protective portion within a single piece of optically clear or visually transparent material that reduces or eliminates the discontinuity between the lenses and frame of conventional eyeglasses. In the preferred embodiment, the unitary construction of the eye protective portion of the device reduces or eliminates impairment of the user's field of view and actually enhances it by providing for unimpeded peripheral vision. A one piece polycarbonate eye protective portion includes a generally rigid front portion that covers the user's eyes and includes a certain amount of flexibility at peripheral portions. The eye protective portion is coupled with the ear protective portion to allow the eye protective portion to move between a "down" position, where the eye protective portion is appurtenant to the user's eyes, and an "up" position, where the eye protective portion is raised up and out of the user's visual field. In this fashion, the ear protective portion of the device remains intact and fully effective against potentially ear damaging noise levels irrespective of whether the eye protective portion is in use or not. In the preferred embodiment, the eye protective portion can also be manufactured in a variety of lenses and in a variety of filters to further enhance the user's visual acuity as desired or required.

The foregoing and other features of the present invention will be apparent from the detailed description that follows.

DETAILED DESCRIPTION

Figure 1:
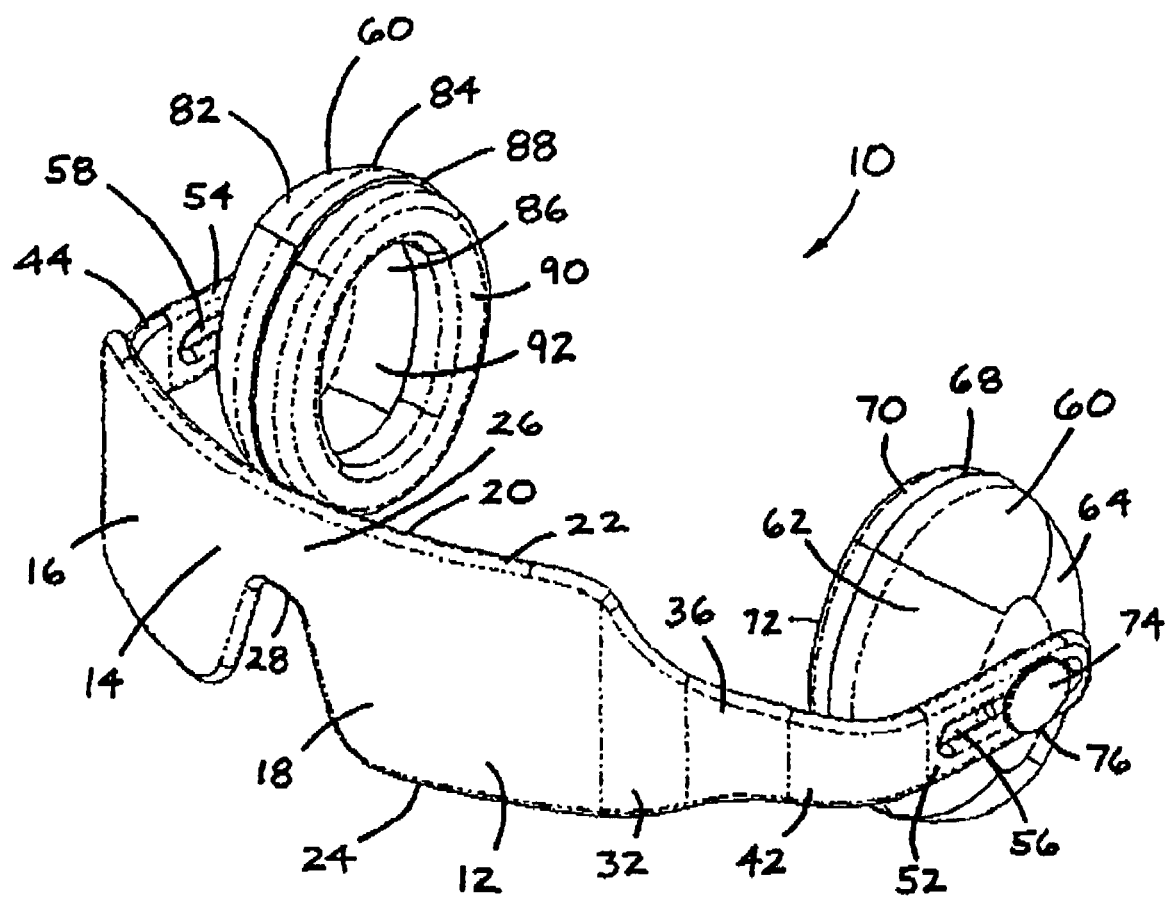
FIG. 1 is a top, front and right side perspective view of an eye and ear protective device constructed in accordance with the present invention.

Referring now to the drawings in detail wherein like numbers represent like elements throughout, FIG. 1 illustrates a perspective view of one embodiment of the eye and ear protective device, generally identified 10, constructed in accordance with the present invention. As shown, the protective device 10 includes the essential elements of an eye protection portion 20 and an ear protection portion 60.

Figure 2:
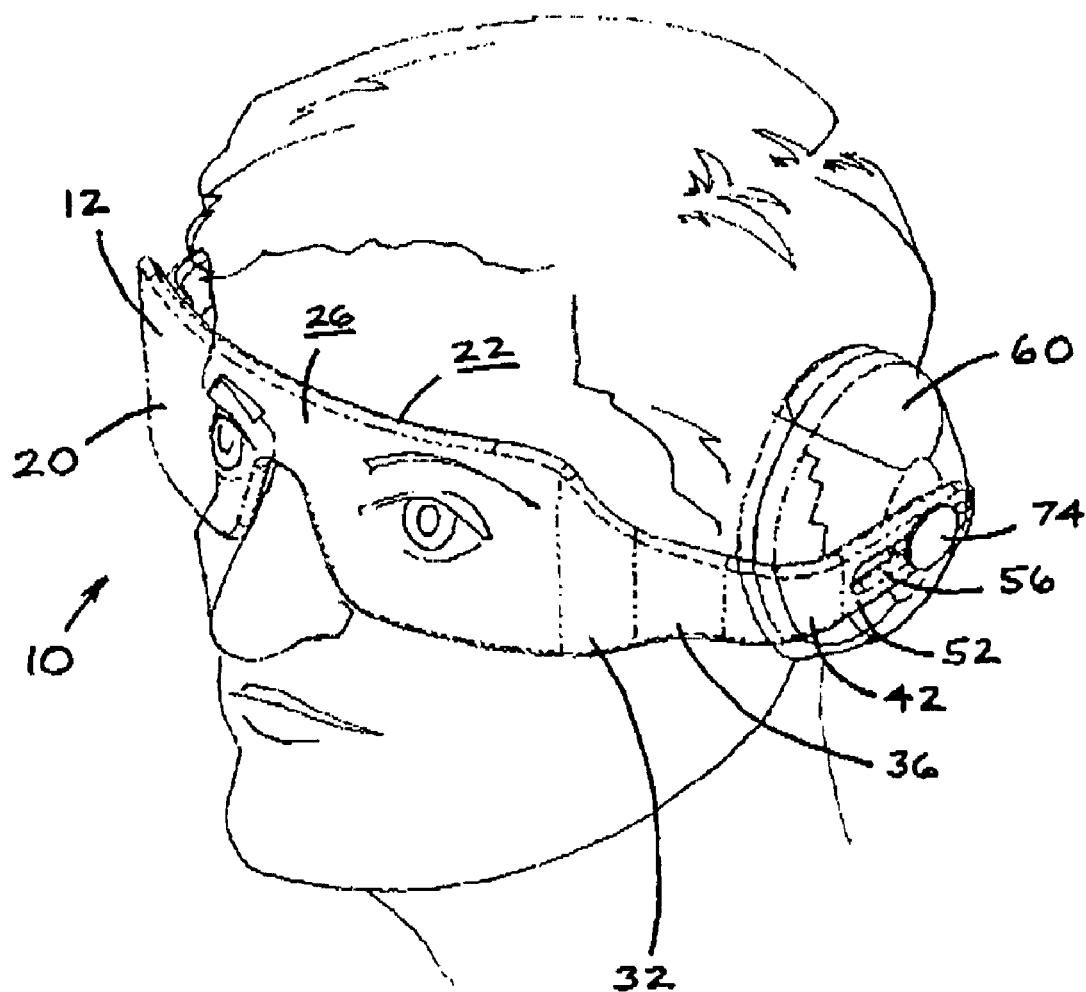
FIG. 2 is a slightly reduced front, top and right side perspective view of the device shown in FIG. 1 and illustrating the device as used.

As shown in FIG. 1, the eye protection portion 20 of the protective device 10 comprises a continuous, substantially planar and symmetrical eye protection member 12. The eye protection member 12 has a frontal portion 14 that is functionally adapted to cover the frontal portion of a user's visual field. See also FIG. 2. This frontal portion 14 includes a pair of optically clear or visually transparent and symmetrical lens portions 16, 18. The lens portions 16, 18 are integrally connected to one another by means of a nose bridge portion 26. The frontal portion is further defined by a top ridge 22 and a bottom ridge 24. A portion of the bottom ridge 24 includes a nose bridge gap 28. The nose bridge gap 28 could include an ancillary nose piece (not shown) for added comfort. Such a nose piece could be removably attachable to the frontal portion 14 and be constructed of a soft neoprene material.

As alluded to earlier, the frontal portion 14 is substantially planar. That does not mean, however, that it is flat. Rather, the preferred embodiment of the present invention contemplates a slight arc or curve to the plane of the frontal portion 14, which arc or curve corresponds very roughly to the contour of a human face. The contour or curve could also correspond roughly to the profile of a pair of prescription glasses worn under the device 10 by the user. Again, reference FIG. 2. The precise shape or curve of the frontal portion 14 is not, however, a limitation of the present invention.

Figure 3:
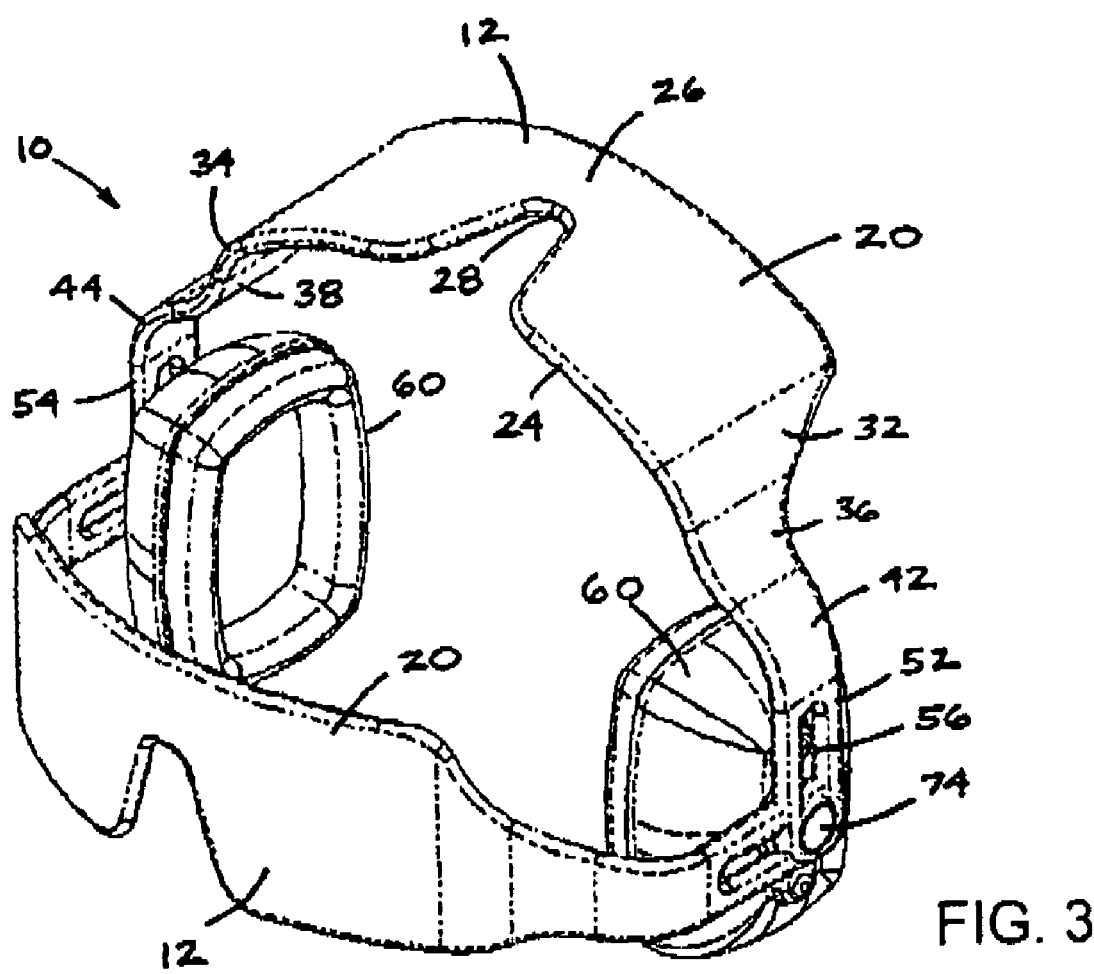
FIG. 3 is a top, front and right side perspective view of another eye and ear protective device constructed in accordance with the present invention and illustrating how the eye protection portion of the device is movable between an "up" position and a "down" position.
Figure 4:
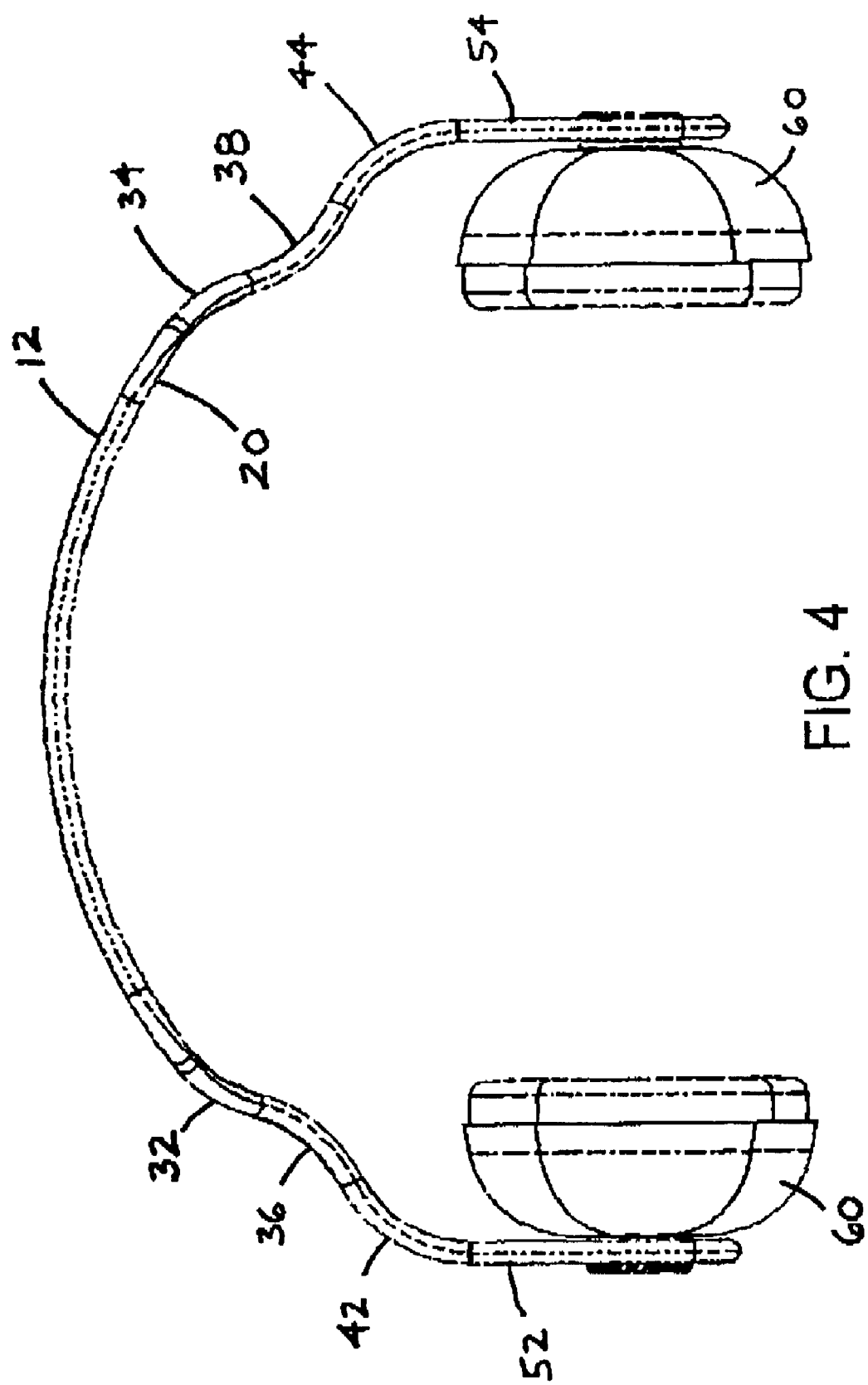
FIG. 4 is a top plan view of the unitary eye protection portion of the device shown in FIG. 1.

Extending outwardly and symmetrically disposed to each side of the frontal portion 14 of the eye protection member 12 of the preferred embodiment is a first substantially planar peripheral portion 32, 34. See also FIG. 3. The plane of each of the first peripheral portions 32, 34 differs from that of the frontal portion 14 and is slightly curved inwardly. Notwithstanding, the first peripheral portions 32, 34 are integrally formed with the frontal portion 14. See also FIG. 4. Outwardly and to each side of the first peripheral portions 32, 34 of the eye protection member 12 is a second substantially planar peripheral portion 36, 38. The plane of each of the second peripheral portions 36, 38 differs from that of the adjacent first peripheral portions 32, 34 and is slightly curved outwardly. As before, the second peripheral portions 36, 38 are also integrally formed with the first peripheral portions 32, 34 to provide a visual continuum therebetween.

Extending outwardly from each of the second peripheral portions 36, 38 of the preferred embodiment is a third and slightly curved peripheral portion 42, 44. Here again, the third peripheral portions 42, 44, together with the first and second peripheral portions 32, 34, 36, 38, respectively, are integrally formed as part of the eye protection member 12 to provide a visual continuum therebetween. The eye protection member 12 includes a pair of backwardly extending and substantially planar distal portions 52, 54. The distal portions 52, 54 of the eye protection member 12 are symmetrical. Disposed within each distal portion 52, 54 is a longitudinally extending slot 56, 58, respectively, the purpose of which will become apparent later in this detailed description.

It is also to be understood that the number of peripheral portions of the eye protection member 12 may be varied, as may the planar or curved shape thereof, without deviating from the scope of the present invention. What is a functional limitation of the invention is the unitary construction of the eye protection member 12. The eye protection member 12 is made from a single piece of material. In the preferred embodiment, that material is a polycarbonate resin material which affords clarity, strength and a certain amount of flexibility. In that preferred embodiment, the frontal portion 14 of the eye protection member 12 is relatively rigid and thick, but not so thick as to provide visual distortion. Outwardly of the frontal portion 14, the peripheral portions of the unitary eye protection member 12 are relatively thinner than the frontal portion 14 so as to allow for greater flex in those peripheral portions. In an alternate embodiment, the frontal portion 14 could be fabricated of a more rigid resin material with support ribs (not shown) defined within it. Other materials may be used, but would need to be optically clear and flexible at the peripheral portions of the eye protection member 12 also.

The ear protection portion 60 of the protective device 10 includes a pair of cup-like ear muff members 62, 82. Each ear muff member 62, 82 is comprised of an outer shell 64, 84 which defines a cavity 86 therewithin. Note that, due to the perspective view of the device 10 shown in FIGS. 1 through 3, the cavity within the one ear muff member 62 is not visible. Each cavity 86 is functionally adapted to receive and cover one of the user's ears. See FIG. 2. The shape of the outer shell 64, 84 of the ear protection portion 60 is not a limitation of the present invention. See, for example, FIG. 3. The outer shell 64, 84 could assume an oval shape, a rounded rectangular shape, or any other shape that is capable of accommodating the human ear without deviating from the scope of the present invention.

Each ear muff outer shell 64, 84 includes an outer shell periphery 68, 88 about which is attached an ear seal 70, 90. The ear seal 70, 90 provides a sound barrier to substantially reduce the amount and level of noise and sound that is able to enter the ear muff cavity 86. Any noise or sound that does penetrate the ear seal 70, 90 is further deadened by the presence of sound insulating foam 92 that is contained within and effectively lines the inner surface of each ear muff cavity 86. Note also that, due to the perspective views shown, the sound insulating foam within the one ear muff member 62 is not visible. Situated on the outer shell 64, 84 of each ear muff member 62, 82, and extending generally perpendicularly outwardly from it, is an extension member 74. Again, the perspective views shown do not illustrate the opposing extension member that extends outwardly from the ear muff member 82. Each extension member 74 terminates in a keeper flange member 76. Each extension member 74 is functionally adapted to cooperatively engage and be slidably received within one of the slots 56, 58 extending longitudinally within the distal portions 52, 54 of the eye protection member 12. The presence of the keeper flange member 76 prevents the extension member 74 from becoming disengaged from the distal portions 52, 54 of the eye protection member 12. It is to be understood that the precise attachment configuration for keeping the distal portions 52, 54 of the eye protection member 12 is not a limitation of the present invention. Other attachment means or configurations could be used without deviating from the scope of the present invention.

In application, the user would grasp the protective device 10 by placing one hand over each of the ear muff members 62, 82. In the preferred embodiment of the present invention, the unitary eye protection member 12 is fabricated of a single piece of material. That material may be a polycarbonate resin material that has elastic "memory" formed within it. That is, the eye protection member 12 may be fabricated such that the distal portions 52, 54 are urged toward one another in the relaxed position. By exerting an outward force on each of the distal portions 52, 54 in order to separate them, there results an opposite force being exerted on each of the ear muff members 62, 82 when the ear muff members 62, 82 are placed onto the user's head and over his or her ears. In this fashion, the protective device 10 may be securely retained on the user's head, positioned over his or her ears. With the protective device 10 in this position, the eye protection member 12 may be adjusted downwardly over the user's eyes and directly in front of his or her forward visual field. In this position, the peripheral portions 32, 34, 36, 38, 42, 44 provide no visual impediment whatsoever. The eye protection member 12 may also be fabricated of a color tinted or light filtering material. The user may adjust the eye protection member 12 upwardly to move it completely out of the user's visual field. See FIG. 3. At all times, the resiliency and material memory of the eye protection member 12 exert a sufficient force on the user's head to maintain the ear protection portion 60 of the device 10 in operable position until removal of the ear muff members 62, 82 is desired or required.

Based upon the foregoing, it will be seen that there has been provided a new and useful combined ear and eye protection device that utilizes the eye protection portion of the device as the head support for the ear protection portion of the device and that configures the unitary eye protection portion in a way that improves on the conventional eyeglass configuration; that provides such a combined ear and eye protection device that configures the eye protection portion in a single piece manufacture and reduces or eliminates the discontinuity between lens and frame; that provides such a combined ear and eye protection device that reduces or eliminates any impairment of the user's field of view and actually enhances it by providing for unimpeded peripheral vision; that provides such a protective device that utilizes a minimal number of elements by incorporating a one piece polycarbonate resin eye protector with a pair of ear muffs and that requires only a minimal number of steps to use; and that provides such a protective device that is easy to assemble, economical to manufacture and that can be manufactured in a variety of lenses.

The invention claimed is:

1. An eye and ear protection apparatus which comprises
   an eye protective portion, said eye protective portion comprising a single piece of flexible eye protective material having elastic memory formed within it and further having a frontal portion and peripheral portions integrally formed with and symmetrically disposed to each side of the frontal portion,
   an ear protective portion, said ear protective portion comprising a pair of cup-like ear-covering members, and
   means for attaching one of the peripheral portions of the eye protective portion directly to one of the ear-covering members of the ear protective portion,
   wherein the position of the eye protective portion is variably and rotatably adjustable relative to the ear protective portion, and
   wherein the ear protective portion is functionally adapted to cover and protect a user's ears and the eye protective portion is functionally adapted to cover and protect a user's eyes.

2. The apparatus of claim 1 wherein the eye protective portion comprises an eye protective member configured in a single piece of optically clear material.

3. The apparatus of claim 2 wherein the eye protective portion is comprised of a polycarbonate resin.

4. The apparatus of claim 3 wherein the eye protective member includes a color tint or a light filtering capacity.

5. A safety device which comprises
   an eye protective portion, the eye protective portion including a frontal portion and at least one peripheral portion disposed symmetrically to each side of the frontal portion, said peripheral portions being integrally formed with the frontal portion in a unitary eye protective member to provide an unobstructed visual field for the user,
   an ear protective portion, the ear protective portion including a pair of opposing ear muff members,
   means for attaching the eye protective portion directive to the ear protective portion, and
   means for variably and rotatably adjusting the position of the eye protective portion relative to the ear protective portion,
   wherein the eye protective portion is the only means for supporting the ear protective portion about a user's head, and
   wherein the eye protective portion supports the ear protective portion such that the ear protective portion covers and protects a user's ears and the eye protective portion covers and protects the user's eyes while in a "down" position, said eye protective portion further being movable to an "up" position.

6. The safety device of claim 5 wherein the eye protective member includes at least one peripheral portion disposed distally symmetrically to each side of the frontal portion, said distally disposed peripheral portions including a slot defined therewithin, wherein the ear protective portion includes a pair of opposing ear muff members, and wherein the attachment and adjustment means comprises a flanged extension member extending outwardly from each ear muff member, said extension member being receivable within the slot of the distally disposed peripheral portion of the eye protective member and being movable therewithin.

7. The safety device of claim 5 wherein the eye protective portion comprises an eye protective member configured in a single piece of visually transparent material.

8. The safety device of claim 5 wherein the eye protective portion comprises an eye protective member configured in a single piece of visually transparent and resilient material.

9. The safety device of claim 5 wherein the eye protective portion comprises an eye protective member configured in a single piece of visually transparent and resilient material, said material comprising a polycarbonate resin.

10. The safety device of claim 5 wherein the eye protective member includes a color tint or a light filtering capacity.

11. An eye and ear safety device which comprises
a unitary eye protective portion comprised of a single piece of optically dear material having a frontal portion and at least one peripheral portion disposed symmetrically to each side of the frontal portion, said peripheral portions providing an unobstructed visual field for the user,
an ear protective portion,
means for attaching the eye protective portion directly to the ear protective portion, wherein the eye protective portion is the only means for supporting the ear protective portion about a user's head, and
means for variably and rotatably adjusting the position of the eye protective portion relative to the ear protective portion,
wherein the eye protective portion supports the ear protective portion such that the ear protective portion covers and protects a user's ears and the eye protective portion covers and protects the user's eyes.

12. The eye and ear safety device of claim 11 wherein the eye protective portion is made of a polycarbonate resin material.

13. The eye and ear safety device of claim 12 wherein the eye protective portion includes a color tint or a light filtering capacity.

* * * * *